US00PP12457P2

(12) United States Plant Patent
Trees

(10) Patent No.: US PP12,457 P2
(45) Date of Patent: Mar. 12, 2002

(54) GERANIUM PLANT NAMED 'BALGALSUSI'

(75) Inventor: Scott C. Trees, Shell Beach, CA (US)

(73) Assignee: Ball FloraPlant, A divison of Ball Horticultural, West Chicago, IL (US)

( * ) Notice: Subject to any disclaimer, the term of this patent is extended or adjusted under 35 U.S.C. 154(b) by 0 days.

(21) Appl. No.: 09/822,006

(22) Filed: Mar. 31, 2001

(51) Int. Cl.[7] ..... A01H 5/00

(52) U.S. Cl. ..... Plt./324
(58) Field of Search ..... Plt./324, 325, 330

*Primary Examiner*—Bruce R. Campell
*Assistant Examiner*—Kent L. Bell
(74) *Attorney, Agent, or Firm*—C. A. Whealy

(57) ABSTRACT

A new and distinct cultivar of Geranium plant named 'Balgalsusi', characterized by its upright and mounded growth habit; freely basal branching habit; dark green leaves with dark brown zonation pattern; and light red-colored semi-double flowers.

1 Drawing Sheet

BACKGROUND OF THE INVENTION

The present invention relates to a new and distinct cultivar of Geranium plant, botanically known as *Pelargonium×hortorum×Pelargonium peltatum,* and hereinafter referred to by the name 'Balgalsusi'.

The new Geranium is a product of a planned breeding program conducted by the Inventor in Arroyo Grande, Calif. The objective of the breeding program was to develop new interspecific Geranium cultivars with freely-branching and cascading growth habits, medium or dark green-colored foliage, large rounded umbels, uniform flowering, and interesting flower and foliage colors.

The new Geranium originated from a self-pollination made by the Inventor of the *Pelargonium×hortorum×Pelargonium peltatum* cultivar 'Sunrise', disclosed in U.S. Plant Pat. No. 10,139. The cultivar 'Balgalsusi' was discovered and selected by the Inventor as a flowering plant within the progeny from this self-pollination in a controlled environment in Arroyo Grande, Calif., in 1998.

Asexual reproduction of the new cultivar by terminal cuttings taken at Arroyo Grande, Calif., has shown that the unique features of this new Geranium are stable and reproduced true to type in successive generations of asexual reproduction.

SUMMARY OF THE INVENTION

The following traits have been repeatedly observed and are determined to be the unique characteristics of 'Balgalsusi'. These characteristics in combination distinguish 'Balgalsusi' as a new and distinct cultivar:

1. Upright and mounded growth habit.
2. Freely basal branching habit.
3. Dark green leaves with dark brown zonation pattern.
4. Light red-colored semi-double flowers.

Plants of the new Geranium differ from plants of the parent cultivar 'Sunrise' in the following characteristics:

1. Plants of the new Geranium have longer internodes than plants of the cultivar 'Sunrise'.

2. Plants of the new Geranium have more umbels but smaller umbels than plants of the cultivar 'Sunrise'.

3. Plants of the new Geranium have longer peduncles than plants of the cultivar 'Sunrise'.

4. Flower color of the new Geranium is slightly lighter than flower color of the cultivar 'Sunrise'.

BRIEF DESCRIPTION OF THE PHOTOGRAPH

The accompanying colored photograph illustrates the overall appearance of the new cultivar, showing the colors as true as it is reasonably possible to obtain in colored reproductions of this type. The photograph comprises a side perspective view of a typical flowering plant of 'Balgalsusi'. Flower and foliage colors in the photograph may differ slightly from the color values cited in the detailed botanical description which accurately describe the colors of the new Geranium.

DETAILED BOTANICAL DESCRIPTION

The cultivar 'Balgalsusi' has not been observed under all possible environmental conditions. The phenotype may vary somewhat with variations in environment such as temperature and light intensity, without, however, any variance in genotype. The following observations, measurements and comparisons describe plants grown 10-cm pots in West Chicago, Ill., under commercial practice in a polycarbonate-covered greenhouse with day temperatures about 20 to 22° C., night temperatures about 18 to 20° C. and light levels about 2,500 to 3,000 foot-candles. Plants used for the photograph and description were about 8 to 10 weeks from planting rooted cuttings. In the following description, color references are made to The Royal Horticultural Society Colour Chart except where general terms of ordinary dictionary significance are used.

Botanical classification: *Pelargonium×hortorum×Pelargonium peltatum* cultivar 'Balgalsusi'.

Parentage:

*Female parent.*—*Pelargonium×hortorum×Pelargonium peltatum* cultivar 'Sunrise', disclosed in U.S. Plant Pat. No. 10,139.

*Male parent.*—*Pelargonium×hortorum×Pelargonium peltatum* cultivar 'Sunrise', disclosed in U.S. Plant Pat. No. 10,139.

Propagation:

*Type cutting.*—Terminal cuttings.

*Time to initiate roots.*—About 7 days at 18° C.

*Time to develop roots.*—About 21 days at 18° C.

*Root description.*—Fibrous, freely branching.

Plant description:

*General appearance.*—Upright and mounded growth habit, eventually somewhat cascading. Appropriate for 10-cm and larger containers.

*Crop time.*—Starting with a rooted cutting, about 8 to 10 weeks are required to produced a finished flowering plant in 10-cm container.

*Growth and branching habit.*—Vigorous and freely basal branching with about 9 lateral branches at the base. Pinching, that is, removal of terminal apices, is typically not required.

*Plant height* (*to top of foliage*).—About 19 cm.

*Plant width.*—About 30 cm.

*Lateral branches.*—Length: About 35 cm. Internode length: About 4.5 cm. Color: 144A.

*Foliage description.*—Leaves simple, generally symmetrical, abundant, opposite. Quantity of leaves per lateral branch: About 14. Length: About 5.5 cm. Width: About 9 cm. Shape: Reniform. Apex: Rounded. Base: Cordate. Margin: Crenate. Venation: Palmate. Texture: Velvety; both surfaces pubescent. Color: Young foliage, upper surface: 143A; zonation pattern, 200A in color and located on the outer half of the leaf. Young foliage, lower surface: 147B. Fully expanded foliage, upper surface: Between 137A and 147A; faint zonation pattern, 200A in color, about 4 mm in width, and located on the outer half of the leaf. Fully expanded foliage, lower surface: 137C. Venation, upper and lower surfaces: 146C. Petiole: Length: About 12 cm. Diameter: About 12 mm. Color: Young leaves, 146C; fully expanded leaves, 146A.

Flower description:

*Flower arrangement and type.*—Light red-colored flowers arranged in hemispherical umbels arising from apical leaf axils. Umbels displayed above the foliage. At full flowering, usually about 6 open umbels and about 4 developing umbels per plant. Flowers semi-double and rounded in shape. Umbels persistent. Flowers not fragrant.

*Flowering season.*—Year-round under greenhouse conditions. In the garden, flowering is continuous from spring until fall.

*Umbels.*—Number of flowers per umbel: About 8. Diameter: About 7.3 cm. Height: About 5.3 cm. Flower diameter: About 5 cm.

*Flower buds.*—Length: About 1.5 cm. Diameter: About 7 mm. Shape: Ovoid. Color: Before showing color, 143A; when showing color, darker than 40A.

*Petals/petaloids.*—Quantity: About 5 petals and about 4 or 6 petaloids per flower. Petaloids variable in size and shape. Arrangement: Imbricate. Petal length: Upper petals: About 3 cm. Lower petals: About 2.5 cm. Petal width: Upper petals: About 1.7 cm. Lower petals: About 1.9 cm. Petal shape: Obovate. Petal/petaloid apex: Rounded. Petal/petaloid base: Attenuate. Petal/petaloid margin: Entire. Petal/petaloid texture: Smooth. Petal/petaloid color: Upper surface: Closest to 40A; venation on upper petals towards base, 53A. Lower surface: Closest to 44C; venation on upper petals, 53B.

*Sepals.*—Quantity: About 5, not imbricate. Length: About 1 cm. Width: About 3 mm. Shape: Ensiform. Apex: Narrowly acute. Margin: Entire. Texture: Pubescent. Color, upper and lower surfaces: 143A overlain with 183A towards base.

*Peduncle* (*umbel stem*).—Length: About 15.3 cm. Angle: Erect to 45° from vertical. Strength: Strong. Texture: Pubescent. Color: Between 144A and 144B.

*Pedicel* (*individual flower stem*).—Length: About 2.1 cm. Angle: Erect. Strength: Strong. Texture: Pubescent. Color: 184A.

*Reproductive organs.*—Androecium: Anther quantity: About 5. Anther size: About 3.2 mm. Anther color: Closest to 86B. Pollen amount: Moderate. Pollen color: Closest to 168A. Gynoecium: Pistil quantity: One. Pistil length: About 1.8 cm. Stigma shape: Five-parted, star-shaped. Stigma color: 60A. Style length: About 9 mm. Style color: 60C.

*Seed.*—Not observed.

Disease resistance: Resistance to pathogens common to Pelargonium has not been observed.

It is claimed:

1. A new and distinct cultivar of Geranium plant named 'Balgalsusi', as herein illustrated and described.

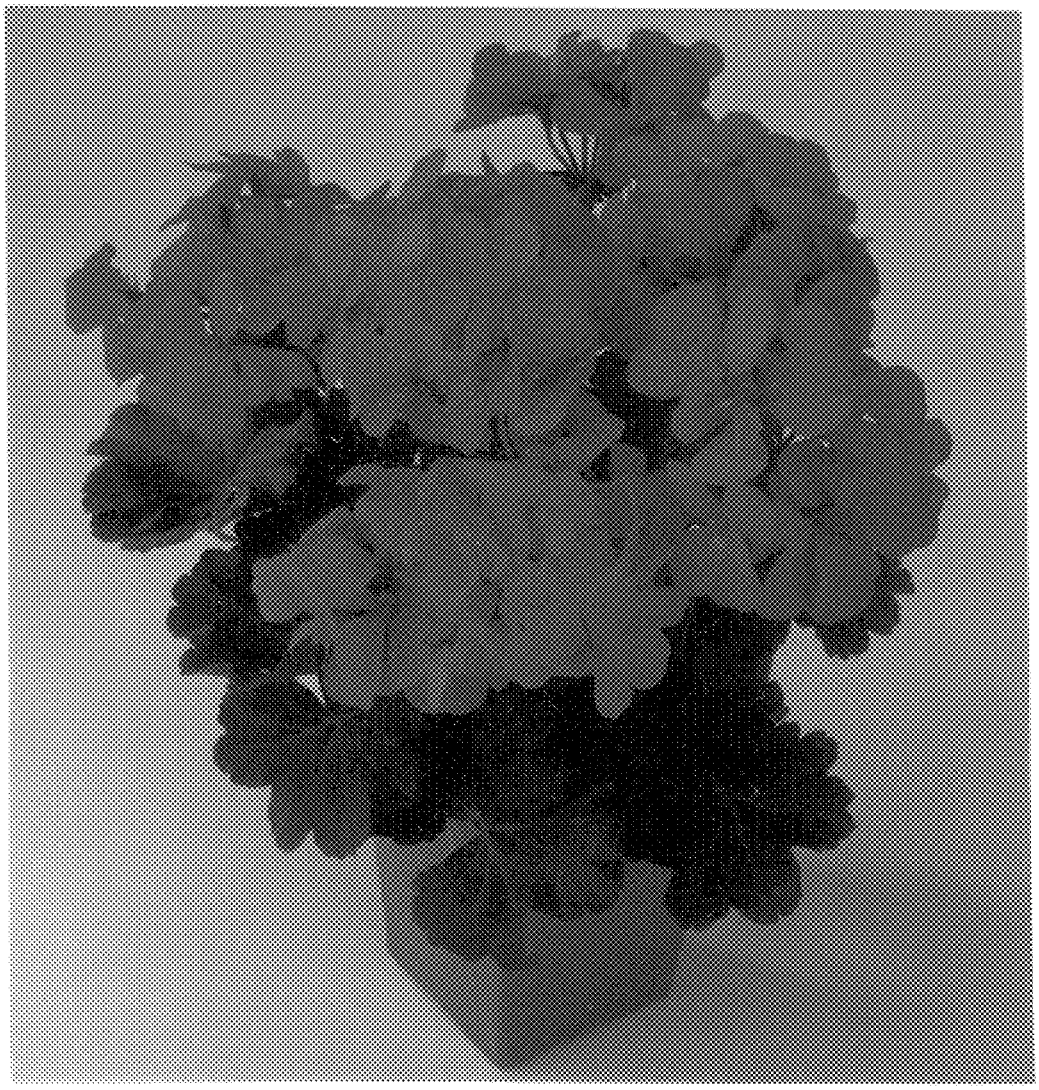

* * * * *